United States Patent
Gardner

(12) 
(10) Patent No.: US 6,302,846 B1
(45) Date of Patent: Oct. 16, 2001

(54) ULTRASOUND METHOD FOR ASSESSING EJECTION FRACTION USING ULTRASOUND CONTRAST AGENTS

(75) Inventor: Edward A. Gardner, San Jose, CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/399,254

(22) Filed: Sep. 20, 1999

(51) Int. Cl.[7] ........................................................ A61B 8/00
(52) U.S. Cl. .................................................................. 600/458
(58) Field of Search ....................................... 600/437, 450, 600/458, 508, 526

(56) References Cited

U.S. PATENT DOCUMENTS 4,572,203 * 2/1986 Feinstein .............................. 600/458
5,735,281 * 4/1998 Rafter et al. ......................... 600/458

* cited by examiner

Primary Examiner—Francis J. Jaworski
(74) Attorney, Agent, or Firm—Brinks Hofer Gilson & Lione

(57) ABSTRACT

The preferred embodiments described herein provide a method for assessing ejection fraction by ultrasonically monitoring a region of a ventricle as contrast agent refills the ventricle following an initial imbalance. In one preferred embodiment, contrast agent is first administered into the body, and then the amount of contrast agent in a ventricle is reduced. In subsequent heart cycles, the ventricle draws contrast-agent-filled blood from the atrium, causing the concentration of contrast agent in the ventricle to increase until it is at equilibrium with the concentration of contrast agent in the atrium. By ultrasonically measuring the increase in contrast agent in the ventricle for one or more heart cycles, ejection faction of the ventricle can be determined without manual or automatic edge detection, assumptions about heart shape, or three-dimensional imaging.

25 Claims, 4 Drawing Sheets

ULTRASOUND METHOD FOR ASSESSING EJECTION FRACTION USING ULTRASOUND CONTRAST AGENTS

BACKGROUND

Ejection fraction is a quantitative way of assessing overall cardiac function. A low ejection fraction can indicate a number of diseases. Quantitative methods of assessing ejection fraction generally require the use of multiple ultrasound planes and edge detection. One accepted technique is to acquire images in orthogonal planes for each heart chamber to be assessed. Tracings of the outline of the chamber in the orthogonal images are used to estimate the chamber volume by assuming an elliptical shape for each image depth. By estimating the volume of the chamber at end of diastole ("ED") and end of systole ("ES"), the ejection fraction can be calculated using the following relation: Ejection Fraction=[1−(Volume at ES)/Volume at ED)]. With a two-dimensional scanner, this technique can be made semi-automatic by automatically detecting the border of the chamber from selected sequences from orthogonal planes and performing the necessary numerical integrations online. This technique can be improved by using additional planes and eliminating the assumption that the heart cross section is elliptical. Because of the required orientation and calculation, this is generally considered only in three-dimensional imaging.

Because this quantitative method requires that volumes be determined, the method functions poorly when the entire heart chamber is poorly visualized. Hypoechoic and anisotropic endocardium and myocardium have long made it difficult to determine the boundary of the heart, especially with hard-to-image patients. In many cases, the boundary of the chamber must be estimated because the endocardium is not visible. Ultrasound contrast agents improve cardiac chamber edge detection, and left ventricular opacification with contrast agents improves ejection fraction measurements using manual or automatic techniques. However, the three-dimensional shape of the heart must still be acquired either through three-dimensional imaging or from assumptions based on orthogonal planes.

Because of the inaccuracy of the manual technique and the low availability of the automated three-dimensional technique, ejection fraction is commonly estimated by eye. In practice, an experienced clinician can generate a number to describe a qualitative assessment of heart function based on viewing several sets of images. This produces an ejection fraction percentage that is widely used in describing heart function and determining treatment. Although assessment of ejection fraction by eye is accepted, scientific physicians prefer to have a truly quantitative method of generating this number. This desire drives the application of edge detection algorithms in cardiology as well as serving as a clinical rational for three-dimensional imaging.

There is a need, therefore, for an improved method for assessing ejection fraction.

SUMMARY

The present invention is defined by the following claims, and nothing in this section should be taken as a limitation on those claims.

By way of introduction, the preferred embodiments described below provide a method for assessing ejection fraction by ultrasonically monitoring a region of a ventricle as contrast agent refills the ventricle following an initial imbalance. In one preferred embodiment, contrast agent is first administered into the body, and then the amount of contrast agent in a ventricle is reduced. In subsequent heart cycles, the ventricle draws contrast-agent-filled blood from the atrium, causing the concentration of contrast agent in the ventricle to increase until it is at equilibrium with the concentration of contrast agent in the atrium. By ultrasonically measuring the increase in contrast agent in the ventricle for one or more heart cycles, ejection fraction of the ventricle can be determined without manual or automatic edge detection, assumptions about heart shape, or three-dimensional imaging.

The preferred embodiments will now be described with reference to the attached drawings.

DETAILED DESCRIPTION OF THE PRESENTLY PREFERRED EMBODIMENTS

Figure 1:
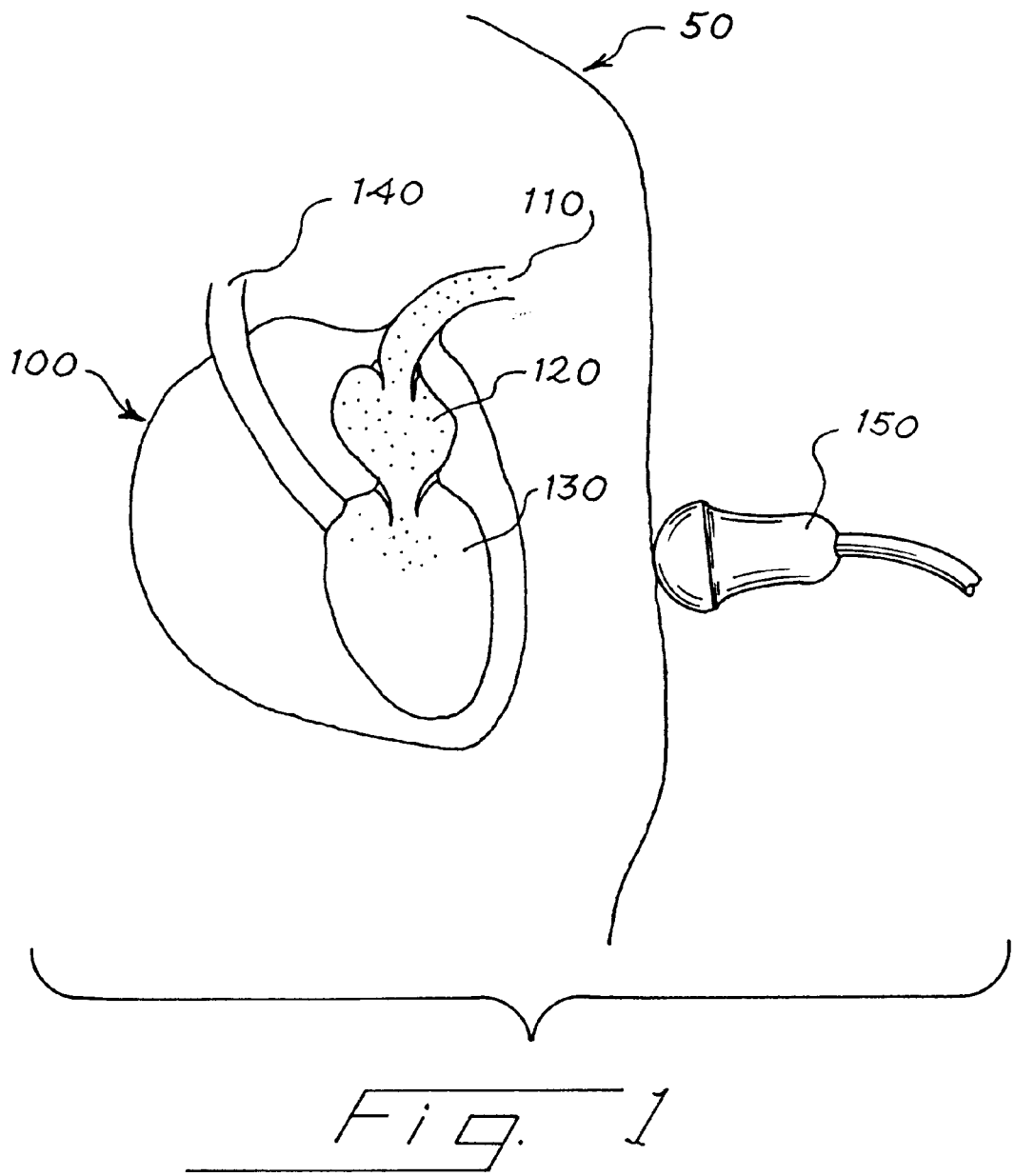
FIG. 1 is a diagram of a heart in a body, which will aid in the illustration of the preferred embodiments.

Turning now to the drawings, FIG. 1 is a diagram of a heart 100 in a body 50, which will aid in the illustration of the preferred embodiments. As shown in FIG. 1, the heart 100 comprises a pulmonary vein 110, a left atrium 120, a left ventricle 130, and an aorta 140. For simplicity, other parts of the heart 100 are not shown. The heart 100 is characterized by a heart cycle having two phases: a diastole phase and a systole phase. During diastole, the left ventricle 130 relaxes and fills with blood from the left atrium 120. During systole, the left ventricle 130 contracts, pumping blood into the aorta 140.

By way of overview, ejection fraction of the left ventricle 130 can be assessed by ultrasonically monitoring the amount of contrast agent refilling the left ventricle 130 after an initial imbalance to determine how rapidly the left ventricle 130 refills. In one preferred embodiment, contrast agent is first administered into the body 50. The concentration of contrast agent in the left ventricle 130 is then reduced so there is less contrast agent in the blood in the left ventricle 130 than in the blood in the left atrium 120. In each heart cycle after the reduction, the left ventricle 130 draws contrast-agent-filled blood from the left atrium 120. This causes the concentration of contrast agent in the left ventricle 130 to increase until it is at equilibrium with the concentration of contrast agent in the left atrium 120. By ultrasonically measuring the increase in contrast agent in the left ventricle 130 for one or more heart cycles, ejection fraction of the left ventricle 130 can be determined.

The reduction of contrast agent and the act of ultrasonically monitoring can be performed with one or more transducers (such as transducer 150) of a medical diagnostic ultrasound system. It should be noted that any appropriate medical diagnostic ultrasound system can be used to implement the preferred embodiments described herein. It is preferred, however, that the medical diagnostic ultrasound system described in "Contrast Agent Imaging with Destruction Pulses in Diagnostic Medical Ultrasound," U.S. patent application Ser. No. 09/348,246, filed Jul. 2, 1999, (which is assigned to the assignee of the present application and is hereby incorporated by reference) be used. As will be appreciated in view of the below description, it is preferred that the ultrasound system be operative to switch between a destructive (continuous) mode and a non-destructive (triggered) mode at the end of systole. In this regard, an ECG system can be coupled to the ultrasound system in order to trigger this transition at the end of systole or at any selected part of the heart cycle.

Figure 2:
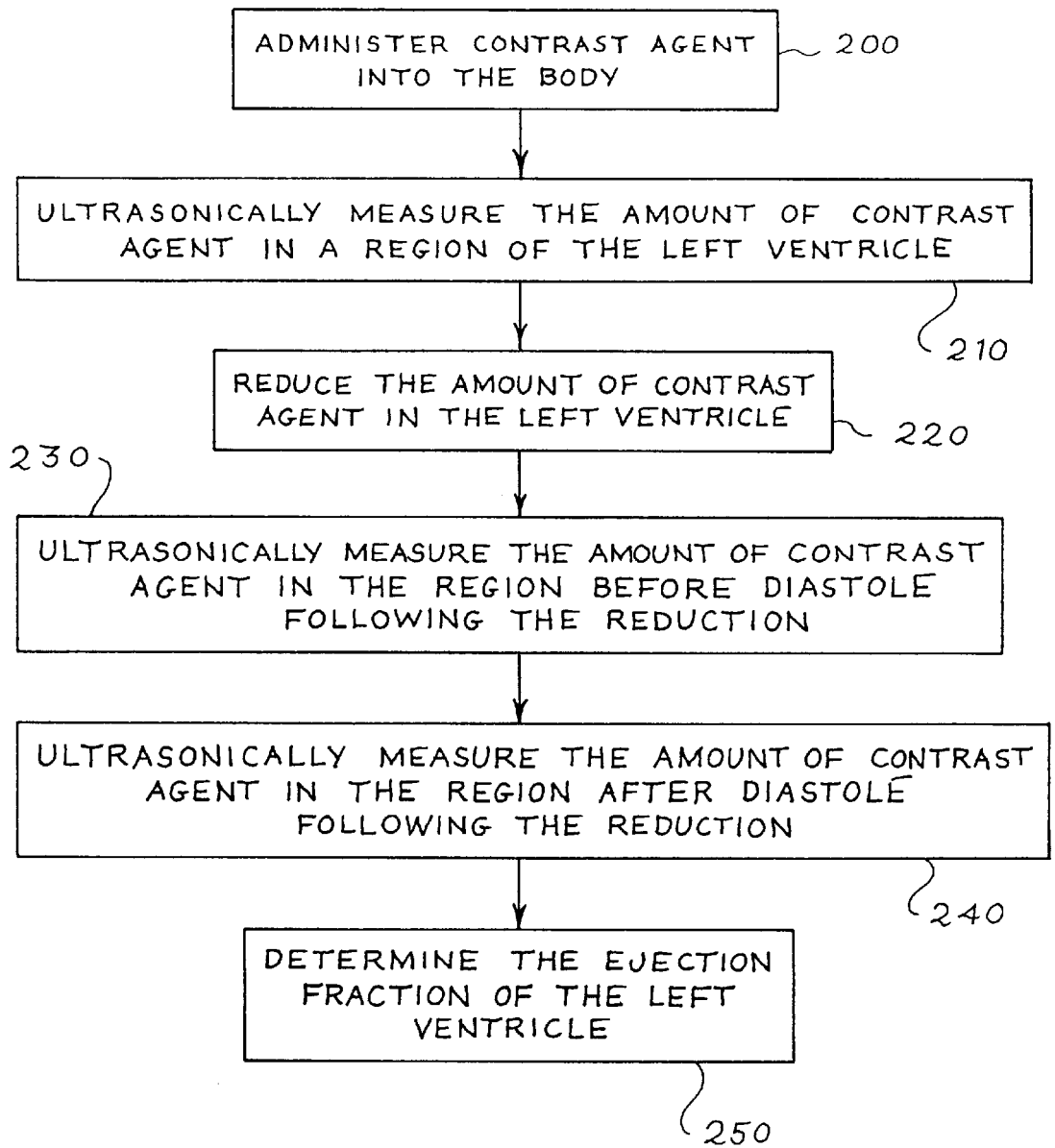
FIG. 2 is a flow chart of a method of a preferred embodiment for assessing ejection fraction.
Figure 3:
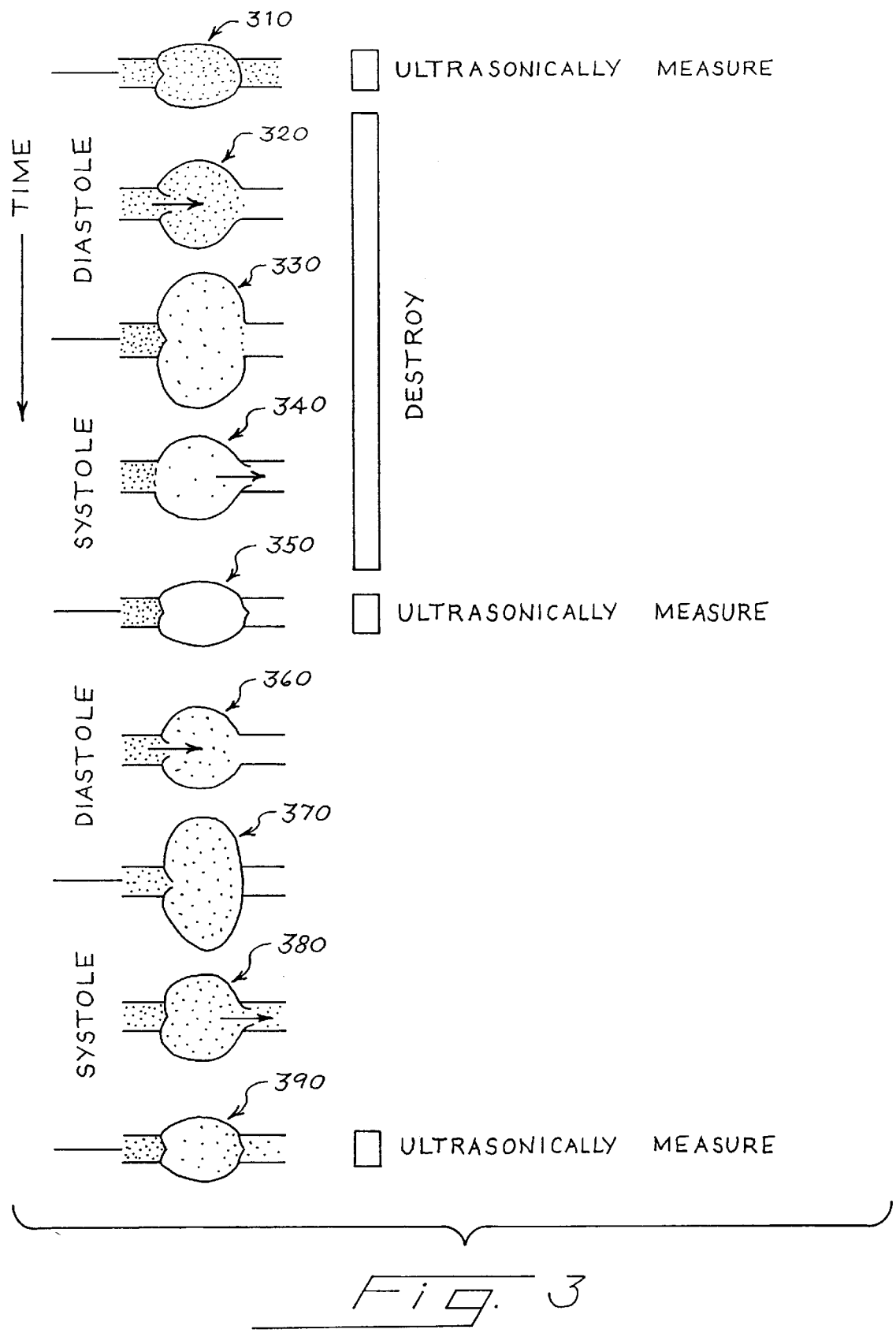
FIG. 3 is an illustration indicating the timing of acts of a method of a preferred embodiment for assessing ejection fraction.

Turning again to the drawings, FIG. 2 is a flow chart of a method of a preferred embodiment for assessing ejection fraction, and FIG. 3 is an illustration of a series of diagrams showing the size of and the amount of contrast agent in the left ventricle at various points in the heart cycle and indicating when in the heart cycle that the acts of this method are performed. The acts of this preferred method will now be described in detail.

Administer Contrast Agent (Block 200)

As shown in FIG. 2, the first act of this preferred method is to administer contrast agent into the body 50 (block 200). One way in which contrast agent can be administered is by venous bolus injection or venous infusion. Although more invasive, contrast agent can also be injected into the right atrium or ventricle. It is preferred that the contrast agent be administered such that the contrast agent is uniformly distributed in most or all of the blood pool or such that the blood entering the left ventricle 130 contain a constant concentration of contrast agent during the ultrasonic monitoring/measuring acts described below.

Ultrasonically Measure the Amount of Contrast Agent in a Region of the Left Ventricle (Block 210)

Next, the amount of contrast agent in a region of the left ventricle 130 is ultrasonically measured (block 210). This provides a measurement of the initial or full concentration of contrast agent in the region. The amount of contrast agent can be ultrasonically measured/monitored by first transmitting and then receiving one or more ultrasonic pulses. By using focused beams and time-gating the receive signal from each pulse, the signal scattered from a specific volume can be isolated. If this volume contains only contrast agents and their concentration is sufficiently low, the scattered energy will be proportional to the number of contrast agent particles in the volume. Other scatters in the volume can also contribute to the received signal, but their contribution can be negated if it is constant between measurements. Because of mixing in the ventricle, the number of contrast agent particles in the measurement volume is a measure of the contrast agent concentration throughout the ventricle. Although a single ultrasound line can be used for this measurement, multiple lines are preferred in order to reduce measurement uncertainty. Multiple lines can be acquired by measuring the backscattered signal from part of an ultrasound image contained in the ventricle 130.

The measuring act can be accomplished with any of a number of techniques (harmonic imaging, pulse inversion, alternating line phase, subharmonic, etc.) With harmonic imaging, the ultrasound system transmits an ultrasonic signal into the region at a first frequency and receives a backscatter signal from the contrast agent in the region at a harmonic or sub-harmonic of the first frequency. The advantage of using harmonic imaging is that background signal from clutter and blood cells is reduced and, accordingly, the dynamic range of the measurement is improved. Background signal is further reduced in pulse inversion by transmitting two pulses of opposite polarity in each measurement direction in quick succession. Analytic summation of the received signals from these pulses causes cancellation of stationary fundamental signal and addition of stationary secondary harmonic signals. A similar result can be attained in the alternating line phase technique with less loss in frame rate by alternating the phase of adjacent transmit lines and forming analytic lines by summation of the received signals. Loss-of-correlation techniques that take advantage of contrast agent destruction can also be used to assess concentration. In these techniques, the difference between multiple pulses fired in quick succession is attributed to the interaction of contrast agents with the ultrasound beam.

In the preferred embodiment shown in diagram 310 of FIG. 3, this measurement takes place before the beginning of diastole. It is preferred that this measurement take place at the same point in the heart cycle as the measurements described below. In one preferred embodiment, the amount of contrast agent is measured after a long quiescent period when the ultrasound system has not been transmitting (e.g., the first frame after long period of Freeze).

Reduce the Amount of Contrast Agent in the Left Ventricle (Block 220)

Next, the amount of contrast agent in the left ventricle 130 is reduced (block 220). It is preferred that the reduction be significant to ensure an accurate assessment of ejection fraction. One way in which contrast agent can be reduced is by destroying or disrupting the contrast agent by rapidly firing ultrasound pulses into the left ventricle 130 during an entire heart cycle (i.e., during both diastole and systole), as shown in diagrams 320, 330, and 340 of FIG. 3.

Because blood containing contrast agent enters the left ventricle 130 during diastole, it is preferred that destruction continue throughout this phase to destroy contrast agent as it enters the ventricle. Destruction can continue through systole to destroy additional contrast agent while no more agent is entering from the atrium. The end of systole (diagram 350) is the preferred time to cease contrast agent destruction and measure the contrast agent concentration (as described below) because this should be the nadir of the contrast agent's concentration.

It is preferred that the destruction pulses be aimed so that no destruction occurs in the other heart chambers. This can be accomplished by carefully selecting the imaging plane. It should be acceptable to destroy contrast agent in the right heart if the destruction is carried out over a short time (e.g., a few heart cycles) because the concentration of contrast agent in the lungs should not be strongly affected. Also, a short axis view of the heart 100 should not destroy contrast agent in the left atrium 120.

It should be noted that any suitable way of reducing the amount of contrast agent can be used. It is preferred, however, that the methods described in "Contrast Agent Imaging with Destruction Pulses in Diagnostic Medical Ultrasound," U.S. patent application Ser. No. 09/348,246, filed Jul. 2, 1999, be used. By way of overview, contrast agent can be destroyed by using high pulse repetition frequency ("HPRF") destruction pulses, which are pulses that are transmitted at a rate faster than required to allow the pulses to propagate to the farthest boundary of a region of interest and return to the transducer 150. Additionally, closely- or widely-spaced multiple transmit beams can be sent out simultaneously. The efficiency of destruction can be increased by changing pulse parameters between the multiple firings of HPRF destruction pulses. For example, by changing the transmit focus, the point of peak intensity changes, thereby varying the location of maximum contrast agent destruction. Additionally, by varying the transmit frequency, penetration into the body 50 can vary and bubbles of various resonating frequencies can be disrupted. Further, increasing pulse power can provide better destruction coverage.

Ultrasonically Measure the Amount of Contrast Agent before Diastole Following the Reduction (Block 230)

Next, before the beginning of diastole following the reduction described above, the amount of contrast agent in the region of the left ventricle 130 is measured (block 230). This provides a measurement of the concentration of contrast agent (if any) in the region after reduction. It is preferred that this measurement be taken at the end of systole (see diagram 350 of FIG. 3) since the measurement described below is also preferably taken at the end of systole.

Ultrasonically Measure the Amount of Contrast Agent after Diastole Following the Reduction (Block 240)

The amount of contrast agent in the region is measured again; this time, after diastole following the reduction described above (block 240). Again, it is preferred that the measurement be made at the end of systole, as shown at 390 in FIG. 3, to provide as much mixing of the contrast agent as possible to ensure uniform distribution of contrast agent in the left ventricle 130. This measurement represents the concentration of contrast agent in the left ventricle 130 after one heart cycle with maximum time for mixing in the left ventricle 130.

Determine the Ejection Fraction of the Left Ventricle (Block 250)

With the measurements made before the reduction of contrast agent, before diastole following reduction, and after diastole following reduction, the ejection fraction of the left ventricle 130 can be determined (block 250). One way in which ejection fraction can be determined is by using the following relationship:

$$E = \frac{C_{ES}(t) - C_{ES}(t-1)}{C_\infty - C_{ES}(t-1)},$$

wherein $C_\infty$ is the steady-state concentration achieved when no contrast agent is destroyed for a long period of time (here, the concentration of contrast agent before the reduction), $C_{ES}(t-1)$ is the concentration of contrast agent before diastole following the reduction, and $C_{ES}(t)$ is the concentration of contrast agent after diastole following the reduction. The derivation of this relationship is provided in Appendix I. To provide a more accurate determination of ejection fraction, it is preferred that a series of measurement be made so that a series of ejection fractions can be calculated and averaged.

As mentioned above, $C_\infty$ is the steady-state concentration achieved when no contrast agent is destroyed for a long period of time. In the preferred method described above, $C_\infty$ was the amount of contrast agent present in the left ventricle 130 immediately before the reduction of contrast agent. Alternatively, the steady-state concentration can be measured at an earlier time before the reduction or following the reduction after contrast agent concentration has reached equilibrium. However, since the steady-state concentration of contrast agent can fluctuate with time, it is preferred that the timing of the measurements described above be used since concentration levels of contrast agent are more stable within a few heartbeats.

There are several advantages associated with these preferred embodiments. First, these preferred embodiments provide a way of assessing ejection fraction without manual or automatic edge detection, assumptions about heart shape, and three-dimensional imaging. Because computer-intensive edge detection algorithms or multiple image planes are not used, these preferred embodiments provide a quick method of assessing ejection fraction. Also, because edge tracing is unnecessary, these preferred embodiments can be used on patients where imaging conditions do not allow the boundary of the entire ventricle to be clearly imaged. Additionally, these preferred embodiments can be used routinely to quantitatively determine ejection fraction in patients that have a venous line for other purposes (e.g., pharmacological stress test) without significantly increasing the time for the examination. Further, these preferred embodiments provide an assessment of ejection fraction that is much more accurate than that produced by eye estimation.

There are several alternative features that can be used with these preferred embodiments. First, although the preferred embodiments were described above in terms of the left ventricle, it is important to note that these preferred embodiments can also be used with the right ventricle. Second, it should be noted that the region can comprise all or part of the left ventricle 130. Preferably, the region does not contain the myocardium, valves, or the right ventricle. The presence of myocardium in the region of interest will introduce error since contrast agent will eventually enter the myocardium and cause it to brighten. However, since the time for this to occur is much longer than that required for the blood to return to the left ventricle 130, the presence of myocardium in the region of interest should produce little error aside from increasing the background (no contrast) signal level.

Figure 4:
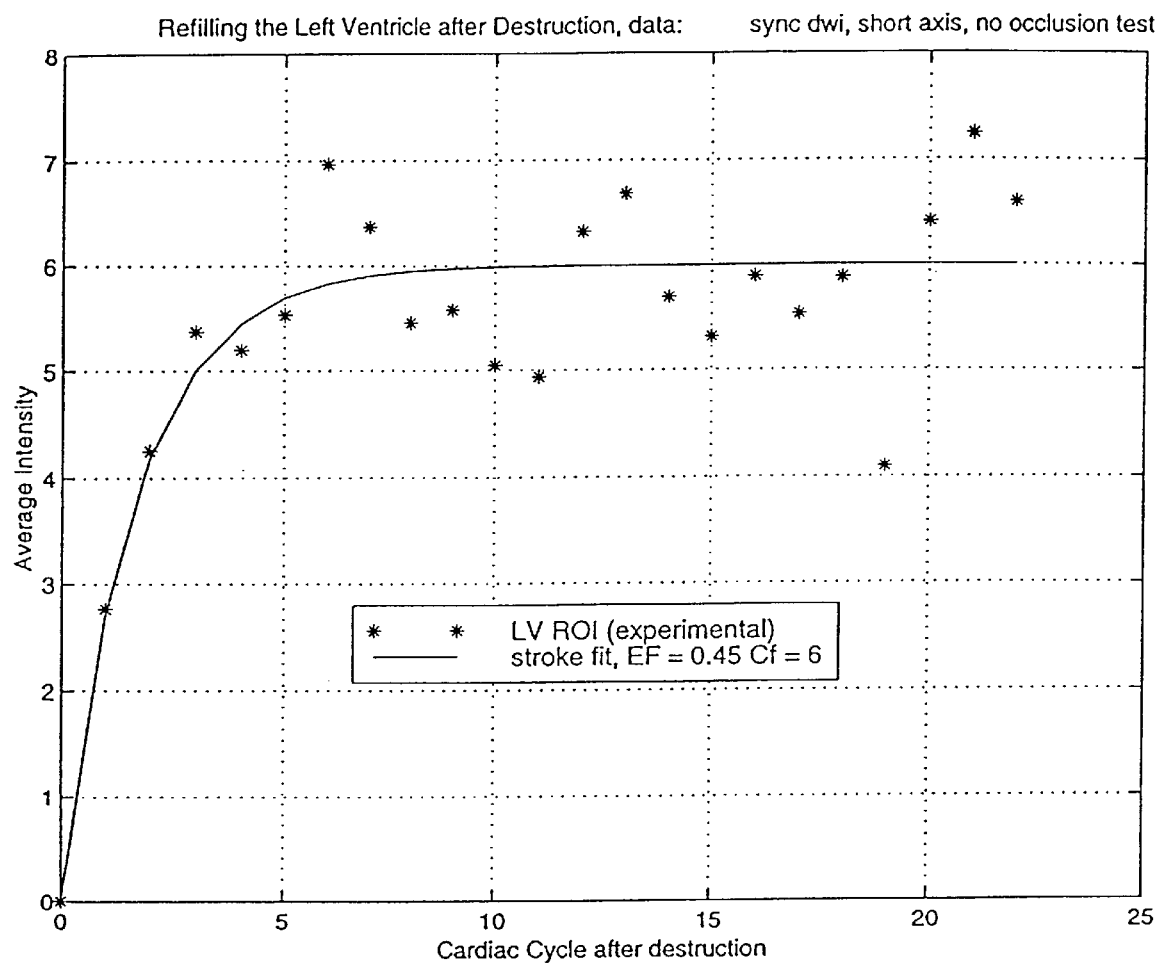
FIG. 4 is a graph of a preferred embodiment showing an average intensity over a number of cardiac cycles following a reduction of contrast agent.

In another preferred embodiment, additional measurements are acquired in order to reduce the statistical variability of the measurement. This can be done by repeating the three-point measurement described above, allowing the equilibrium concentration to be reached between measurements. Alternatively, if a substantially non-destructive technique is used to measure the contrast agent concentration, measurements can be made after multiple heart cycles following contrast agent destruction. Subsets of these measurements can be used to make separate estimates of the ejection fraction, or the entire set can be fit with a curve using a least-square or similar technique. The resulting curve is characterized by the equilibrium concentration, the initial (post-reduction) concentration, and the ejection fraction. One or more measurements of the amount of contrast agent present before reduction can also be made to enhance the accuracy of this approach. As an example of this alternate embodiment, consider FIG. 4, which shows an average intensity of pixels in an imaged region of the left ventricle 130 over a number of cardiac cycles following the reduction of contrast agents. The form of this curve is similar to the solution to a dye-dilution-type differential equations: $A-B^* (\exp(-t/\tau))$. However, because of the stroke nature of flow in the heart, the time constant, $\tau$, is only equal to the reciprocal of the ejection fraction for very small ejection fractions.

In a further alternate embodiment, instead of using destruction to set up an imbalance between the left ventricle 130 and the left atrium 120, a rapid bolus injection can be used to set up the imbalance. Provided regions of interest can be placed in both the left atrium 120 and the left ventricle 130 without a significant amount of contrast agent between the region of interest and the transducer 150 (to eliminate attenuation effects), the concentration in both chambers can be monitored. The delay for the contrast agent to fill the left ventricle 130 after it fills the left atrium 120 will indicate the ejection fraction of the left ventricle 130.

In yet another alternate embodiment, instead of using a medical diagnostic imaging system, an imaging system of another modality (e.g., an x-ray system) that is sensitive to contrast agents or another appropriate agent can be used.

It is important to note that any of the various aspects of the preferred embodiments can be used alone or in combination. Additionally, it is preferred that the ultrasound system perform the embodiments described above using any appropriate software and/or hardware components. It should be understood that any appropriate hardware, analog or digital, and any appropriate software language can be used. Additionally, the methods described above can be implemented exclusively with hardware.

It is intended that the foregoing detailed description be understood as an illustration of selected forms that the invention can take and not as a definition of the invention. It is only the following claims, including all equivalents, that are intended to define the scope of this invention.

APPENDIX I

The contrast agent mass in the left ventricle can be calculated as: $P_{ES}(t)=P_{ED}(t-1)[1-E]$, where $P_{ES}(t)$ is the contrast agent mass in the left ventricle at the end of systole, $P_{ED}(t-1)$ is the contrast agent mass in the left ventricle immediately preceding systole at time t, and E is the left ventricle's ejection fraction.

Further, $P_{ED}(t-1)=P_{ES}(t-1)+P_s$, where $P_s$ is the contrast agent mass that enters during one stroke of the heart and $P_{ES}(t-1)$ is the mass at the end of systole immediately preceding the diastole in question.

Combining these equations yields:

$$P_{ES}(t)=(1-E)\{P_{ES}(t-1)+P_s\}$$

The contrast concentration is given by, $$C_{ES}(t) = (1-E)\left\{C_{ES}(t-1) + \frac{P_s}{V_{ES}}\right\},$$

where
$V_{ES}$ is the end systole volume of the left ventricle.
The stable condition defined for $P_s/V_{es}$=constant is $$C_\infty = \frac{P_s}{V_{stroke}} = \frac{P_s}{V_{ED}-V_{ES}} = \frac{P_s}{V_{ES}(V_{ED}/V_{ES}-1)} = \frac{P_s(1-E)}{EV_{ES}}$$

where $V_{ed}$ is the end diastolic volume of the left ventricle.
Identifying $C_\infty$ in the above equation for $C_{es}(t)$ yields $$C_{ES}(t)=(1-E)C_{ES}(t-1)+EC_\infty.$$

This can be solved for E, yielding:

$$E = \frac{C_{ES}(t) - C_{ES}(t-1)}{C_\infty - C_{ES}(t-1)}$$

What is claimed is:

1. A method for assessing ejection fraction of a ventricle with a medical diagnostic ultrasound system, the ventricle having a reduced amount of contrast agent, the method comprising the acts of:
   (a) ultrasonically measuring an amount of contrast agent in a region of the ventricle over a plurality of heart cycles after a reduction of contrast agent in the ventricle; and
   (b) determining an ejection fraction of the ventricle using the amounts of contrast agent measured in (a).

2. The method of claim 1 further comprising ultrasonically measuring an amount of contrast agent in a region of the ventricle before the reduction of contrast agent in the ventricle, and wherein (b) comprises determining an ejection fraction of the ventricle using the amounts of contrast agent measured in (a) and the amount measured before the reduction of contrast agent in the ventricle.

3. The method of claim 1 further comprising administering a contrast agent to a body.

4. The method of claim 1, wherein the region comprises a part of the ventricle.

5. The method of claim 1, wherein the region comprises an entire ventricle.

6. The method of claim 1, wherein (a) comprises:
   (a1) transmitting an ultrasonic signal into the region of the ventricle at a first frequency; and
   (a2) receiving a backscatter signal from the region of the ventricle at a harmonic of the first frequency.

7. The method of claim 1, wherein (a) comprises synchronizing the act of ultrasonically measuring with a portion of a heart cycle.

8. The method of claim 7, wherein the heart is characterized by a heart cycle comprising an end of systole, and wherein (a) comprises synchronizing the act of ultrasonically measuring with the end of systole.

9. The method of claim 1, wherein the ventricle comprises a left ventricle.

10. The method of claim 1, wherein the ventricle comprises a right ventricle.

11. A method for assessing ejection fraction of a ventricle with a medical diagnostic ultrasound system, the ventricle having a reduced amount of contrast agent, the method comprising the acts of:
   (a) ultrasonically measuring a first amount of contrast agent in a region of a ventricle of a heart before a reduction of contrast agent in the ventricle;
   (b) ultrasonically measuring a second amount of contrast agent in the region, the measurement being made after the reduction of contrast agent in the ventricle and before diastole following the reduction of contrast agent in the ventricle;
   (c) ultrasonically measuring a third amount of contrast agent in the region, the measurement being made after diastole following the reduction of contrast agent in the ventricle; and
   (d) determining an ejection fraction of the ventricle using the first, second, and third measured amounts of contrast agent.

12. The method of claim 11, wherein the measurements of (a), (b), and (c) are taken at an end of systole.

13. The method of claim 11 further comprising administering a contrast agent to a body.

14. The method of claim 11, wherein the region comprises a part of the ventricle.

15. The method of claim 11, wherein the region comprises an entire ventricle.

16. The method of claim 11, wherein at least one of the measuring acts comprises:
   transmitting an ultrasonic signal into the region of the ventricle at a first frequency; and
   receiving a backscatter signal from the region of the ventricle at a harmonic of the first frequency.

17. The method of claim 11, wherein the ventricle comprises a left ventricle.

18. The method of claim 11, wherein the ventricle comprises a right ventricle.

19. A method for assessing ejection fraction of a ventricle with a medical diagnostic ultrasound system, the ventricle having a reduced amount of contrast agent, the method comprising the acts of:
  (a) ultrasonically monitoring contrast agent refilling a region of a ventricle of a heart after a reduction of contrast agent in the ventricle; and
  (b) assessing ejection fraction of the ventricle.

20. The method of claim 19 further comprising administering a contrast agent to a body.

21. The method of claim 19, wherein the region comprises a part of the ventricle.

22. The method of claim 19, wherein the region comprises an entire ventricle.

23. The method of claim 19, wherein the act of ultrasonically monitoring is synchronized with a portion of a heart cycle.

24. The method of claim 19, wherein the ventricle comprises a left ventricle.

25. The method of claim 19, wherein the ventricle comprises a right ventricle.

* * * * *